United States Patent
Takahashi et al.

(10) Patent No.: US 11,766,497 B2
(45) Date of Patent: Sep. 26, 2023

(54) STERILIZING METHOD AND STERILIZER

(71) Applicant: MIURA CO., LTD., Matsuyama (JP)

(72) Inventors: Yuichi Takahashi, Matsuyama (JP); Tomoyuki Mizobe, Matsuyama (JP); Kenichi Matsuo, Tokyo (JP); Junji Yamamura, Tokyo (JP); Yasuo Nakamura, Tokyo (JP)

(73) Assignee: MIURA CO., LTD., Matsuyama (JP)

( * ) Notice: Subject to any disclaimer, the term of this patent is extended or adjusted under 35 U.S.C. 154(b) by 291 days.

(21) Appl. No.: 17/178,723

(22) Filed: Feb. 18, 2021

(65) Prior Publication Data
US 2021/0299312 A1 Sep. 30, 2021

(30) Foreign Application Priority Data
Mar. 27, 2020 (JP) .................... 2020-057992

(51) Int. Cl.
*A61L 9/015* (2006.01)
*A61L 2/20* (2006.01)

(52) U.S. Cl.
CPC .............. *A61L 9/015* (2013.01); *A61L 2/202* (2013.01); *A61L 2202/122* (2013.01); *A61L 2202/13* (2013.01)

(58) Field of Classification Search
CPC ..... A61L 9/015; A61L 2/202; A61L 2202/122
See application file for complete search history.

(56) References Cited

U.S. PATENT DOCUMENTS

| 2008/0233002 A1* | 9/2008 | Mizuno .................. A61L 2/202 422/22 |
| 2011/0008209 A1 | 1/2011 | Lee |
| 2011/0076192 A1 | 3/2011 | Robitaille et al. |
| 2011/0280765 A1* | 11/2011 | Hirose .................. A61L 2/202 422/168 |
| 2013/0105025 A1 | 5/2013 | Fehr et al. |
| 2018/0353633 A1* | 12/2018 | Laflamme ................ A61L 2/24 |

FOREIGN PATENT DOCUMENTS

| JP | 11-347106 A | 12/1999 |
| JP | 2002-360672 A | 12/2002 |
| JP | 2010-532198 A | 10/2010 |
| JP | 5480975 B2 | 2/2013 |
| JP | 2016-120078 A | 7/2016 |
| JP | 2016-154835 A | 9/2016 |
| JP | 2017-18267 A | 1/2017 |
| WO | 2005/094907 A1 | 10/2005 |

(Continued)

OTHER PUBLICATIONS

Office Action for U.S. Appl. No. 17/178,723, dated Mar. 30, 2023, the patent application is related to U.S. Appl. No. 17/178,723.

(Continued)

*Primary Examiner* — Sean E Conley
*Assistant Examiner* — Justin Hwang
(74) *Attorney, Agent, or Firm* — Kenichiro Yoshida

(57) ABSTRACT

A sterilizing method for sterilizing a sterilization object housed in a chamber 11 includes an ozone preparation step S504 for filling an inside of a buffer tank 34 with ozone gas, and an ozone injection step S505 for injecting the ozone gas filled in the inside of the buffer tank 34 into the chamber 11.

2 Claims, 11 Drawing Sheets

(56) References Cited

FOREIGN PATENT DOCUMENTS

| | | | |
|---|---|---|---|
| WO | WO-2009005252 A2 * | 1/2009 | ............. A61L 2/202 |
| WO | 2011038487 A1 | 4/2011 | |

OTHER PUBLICATIONS

Office Action for U.S. Appl. No. 17/178,723, dated Jun. 6, 2023, the patent application is related to U.S. Appl. No. 17/178,723.
Office Action for Chinese Patent Application No. 201980080296.3, dated May 12, 2023, the patent application corresponds to related U.S. Appl. No. 17/292,950.

* cited by examiner

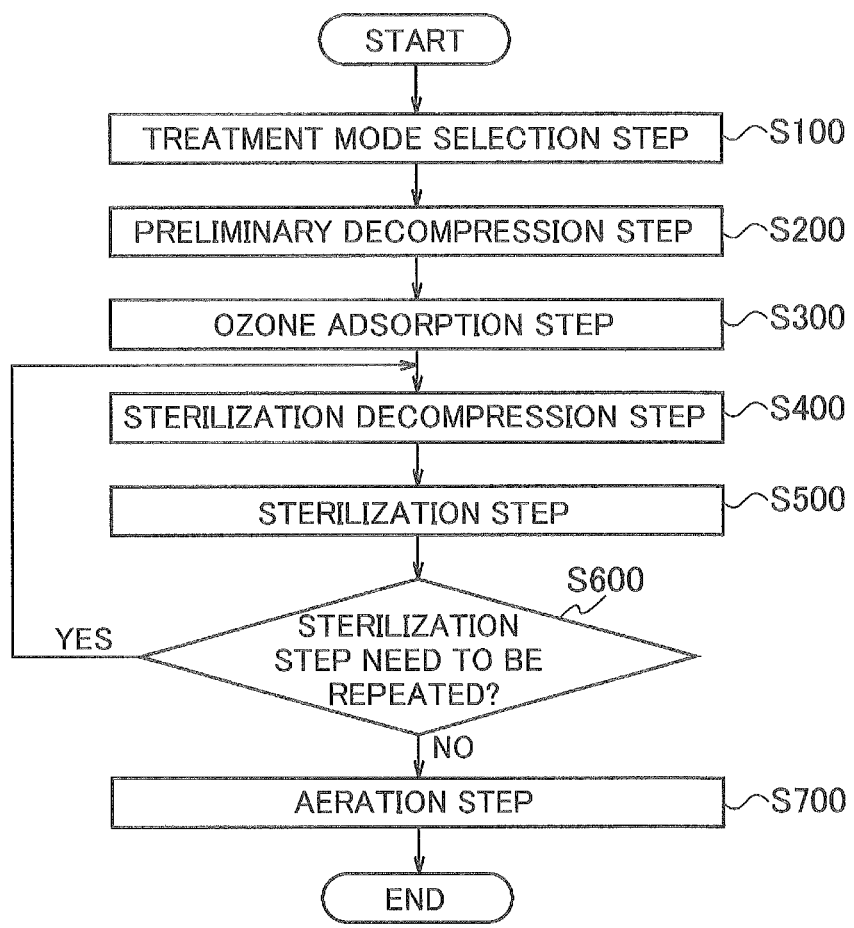

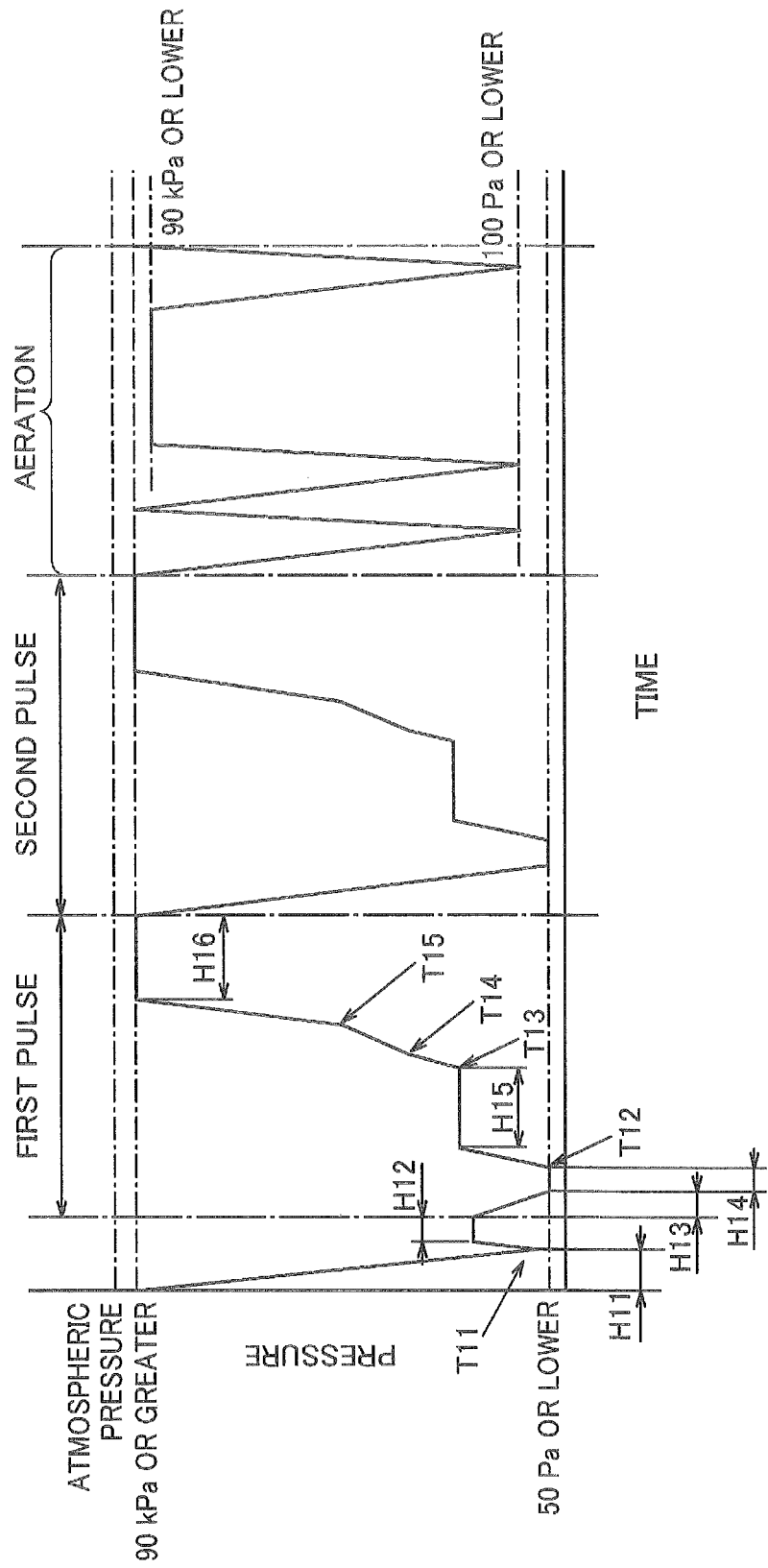

FIG. 4

| TREATMENT MODE | OBJECT TO BE STERILIZED | TREATMENT TIME | INJECTION AMOUNT OF AQUEOUS SOLUTION OF HYDROGEN PEROXIDE (PER PULSE) | EXPOSURE TIME (PULSE NUMBER) |
|---|---|---|---|---|
| SHORT MODE | MEDICAL INSTRUMENT WITH NO DUCT PART (SURFACE STERILIZATION) | ABOUT 30 MINUTES | x1%:y1ml<br>x2%:y2ml | 2 PULSES |
| NORMAL MODE | MEDICAL INSTRUMENT WITH NO DUCT PART (SURFACE STERILIZATION) | ABOUT 50 MINUTES | THE SAME AS ABOVE | 2 PULSES |
| LONG MODE | MEDICAL INSTRUMENT MADE OF STAINLESS STEEL WITH DUCT PART (HARD ENDOSCOPE AND THE LIKE) | ABOUT 60 MINUTES | x1%:y1ml<br>x1%:y3ml | 2 PULSES |

FIG. 7

| | COMPARATIVE EXAMPLE 1 | COMPARATIVE EXAMPLE 2 | EXAMPLE |
|---|---|---|---|
| INJECTION AMOUNT OF HYDROGEN PEROXIDE (FIRST AQUEOUS SOLUTION) | 0.5ml | 0.5ml | 0.5ml |
| KEEPING TIME OF HYDROGEN PEROXIDE (FIRST AQUEOUS SOLUTION) | 2 TO 3 MINUTES | 2 TO 3 MINUTES | 2 TO 3 MINUTES |
| OZONE INJECTION AMOUNT | 0.07g | NONE | 0.07g |
| OZONE BUFFER INJECTION TIME | 1 MINUTE × 4 g/h | — | 1 MINUTE × 4 g/h |
| PURE WATER INJECTION AMOUNT | NONE | NONE | 5ml |
| AIR INJECTION | NONE | EXECUTED (−10 kPa) | NONE |
| FINAL KEEPING TIME | 5 MINUTES | 7 MINUTES | 5 MINUTES |
| EXPOSURE TIME | 1 PULSE | 1 PULSE | 1 PULSE |
| STERILIZATION KEEPING TIME (TOTAL STERILIZATION TREATMENT TIME) | ABOUT 11 MINUTES | ABOUT 11 MINUTES | ABOUT 11 MINUTES |

FIG. 8

|  | NEGATIVE RATE | |
|---|---|---|
| COMPARATIVE EXAMPLE 1 | 3/13 (1/3, 0/5, 2/5) | 23% |
| COMPARATIVE EXAMPLE 2 | 2/13 (1/3, 0/5, 2/5) | 15% |
| EXAMPLE | 13/13 (3/3, 5/5, 5/5) | 100% |

STERILIZING METHOD AND STERILIZER

TECHNICAL FIELD

The present disclosure relates to a sterilizing method and a sterilizer.

BACKGROUND ART

Reusable medical instruments used for surgical operations and medical cares in hospitals are subjected to treatment of sterilization after sufficient cleaning in order to remove adhesive matter such as blood and protein.

A sterilizing method is known that uses hydrogen peroxide as main sterilization gas and further uses additional gas for executing such sterilization treatment in order to improve the sterilization efficiency. Patent Literature 1 discloses sterilizing method and apparatus that execute a series of steps of reducing a pressure in a chamber housing an object to be sterilized, injecting vapor of an aqueous solution of hydrogen peroxide for sterilization to keep the state, and further injecting ozone gas for sterilization to keep the state.

CITATION LIST

Patent Literature

Patent Literature 1: Japanese Patent No. 5480975

SUMMARY OF THE INVENTION

The sterilizing apparatus disclosed in Patent Literature 1 injects the ozone gas produced by an ozone generator directly to the inside of the chamber via a pipe. In view of diffusibility of the ozone gas for enhancing uniform diffusion of the ozone gas inside the chamber, the ozone generator may need to have high output performance so as to improve the diffusibility. Increasing a size of the entire ozone generator may deal with the improvement in the diffusibility, but at the same time, inevitably leads to an increase in size of the sterilizing apparatus accordingly.

An object of the present disclosure is to provide a sterilizing method and a sterilizer capable of improving diffusibility of ozone gas inside a chamber while avoiding an increase in size of the apparatus.

Solution to Problem

A first aspect of the present disclosure provides a sterilizing method for sterilizing a sterilization object housed in a chamber, the method including an ozone preparation step of filling an inside of a buffer tank with ozone gas, and an ozone injection step of injecting the ozone gas filled in the inside of the buffer tank to an inside of the chamber.

The sterilizing method may also include a first vapor preparation step of evaporating and filling a first aqueous solution of hydrogen peroxide in an evaporator, and a first vapor injection step of injecting produced vapor to the inside of the chamber from the evaporator. The sterilizing method may further include a second vapor preparation step of evaporating and filling, in the evaporator, a second aqueous solution of hydrogen peroxide, water in which pyrogen is removed or inactivated, water in which bacteria or microbes are removed or inactivated, or a solution containing a volatile compound, and a second vapor injection step of injecting produced vapor to the inside of the chamber from the evaporator.

A second aspect of the present disclosure provides a sterilizer including a chamber configured to house a sterilization object, an ozone generator configured to produce ozone gas, a buffer tank configured to communicate with the chamber and to be filled with the ozone gas produced by the ozone generator, and a controller configured to control an operation of injecting the ozone gas filled in the buffer tank to an inside of the chamber.

Advantageous Effects

The present disclosure can provide a sterilizing method and a sterilizer capable of improving diffusibility of ozone gas inside a chamber while avoiding an increase in size of the apparatus.

BRIEF DESCRIPTION OF DRAWINGS

FIG. 2 is a flowchart showing a process of sterilizing method according to the first embodiment.

FIG. 3 is a graph showing a change in pressure inside a chamber according to the first embodiment.

FIG. 4 is a table showing plural processing modes executed by the sterilizer according to the first embodiment.

FIG. 7 is a table showing various kinds of conditions used for a sterilization treatment test according to the second embodiment.

FIG. 8 is a table showing results of the sterilization treatment test executed under the conditions shown in FIG. 7.

DESCRIPTION OF EMBODIMENTS

Figure 1:
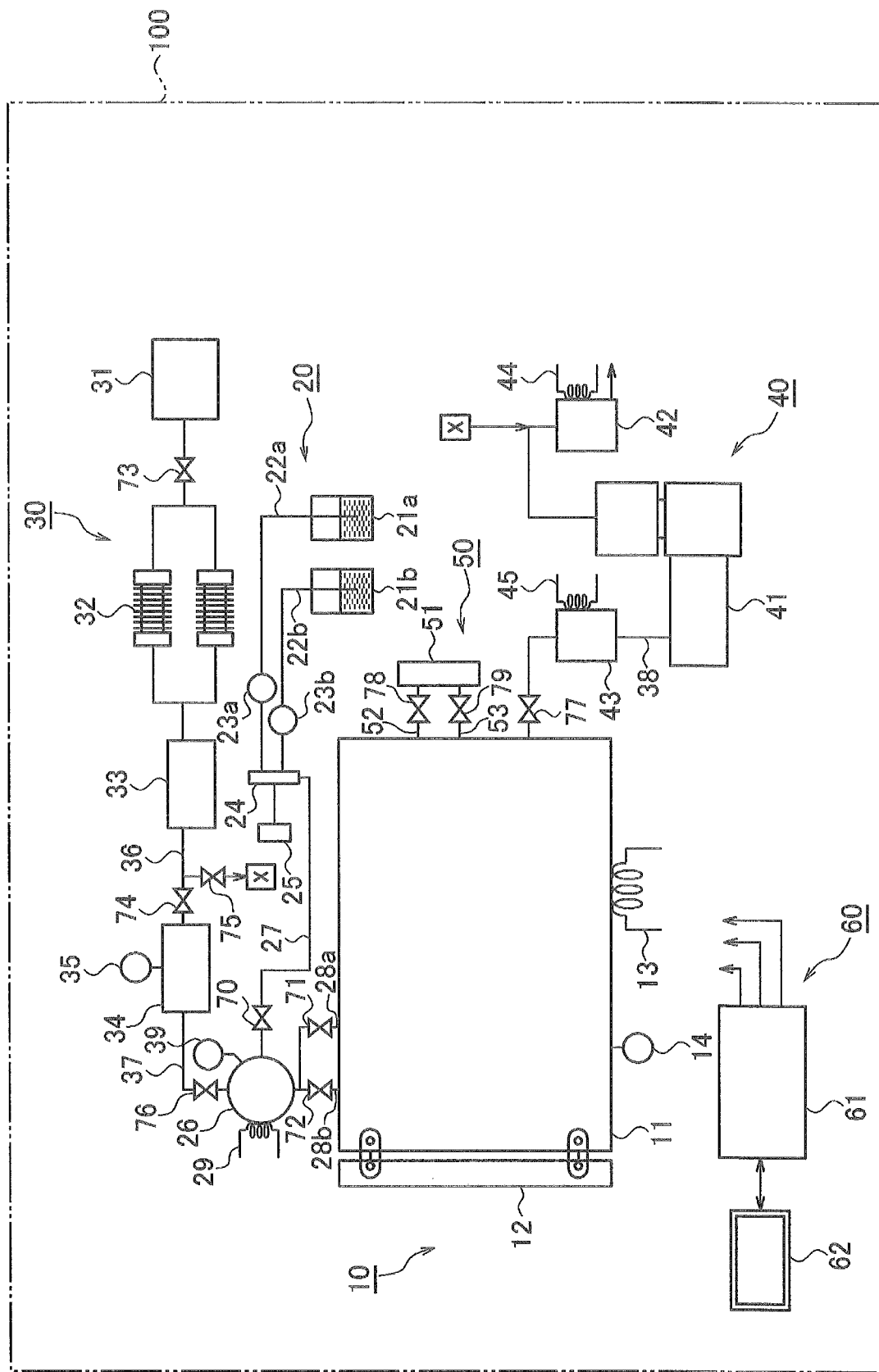
FIG. 1 is a schematic diagram showing a configuration of a sterilizer according to a first embodiment of the present disclosure.

Embodiments of the present disclosure will be described in detail below with reference to the drawings. The following dimensions, materials, and specific numerical values described in the respective embodiments are indicated for illustration purposes, and the present disclosure is not intended to be limited thereto unless otherwise specified. The elements having substantially the same functions and structures illustrated below are designated by the same reference numerals, and overlapping explanations are not made below. The elements described below but not related directly to the present disclosure are not shown in the drawings.

First Embodiment

FIG. 1 is a schematic diagram showing a configuration of a sterilizer 100 according to a first embodiment. The sterilizer 100 sterilizes an object to be sterilize by use of sterilization gas. Materials mainly included in the sterilization gas used in the present embodiment are hydrogen peroxide ($H_2O_2$) and ozone ($O_3$).

The object to be sterilized is herein presumed to be a medical instrument used in a hospital for surgical operations and medical cares and brought into contact with a blood circulatory system or aseptic tissues. Examples of medical instruments include a heat-resistant steel product such as a pair of forceps, a surgical tweezer, and surgical scissors, and a non-heat resistant resin product such as a hard endoscope made of stainless steel used for laparoscopic surgery, a soft endoscope used for bronchial or urinary surgery, and a power supply cable as an attachment for these endoscopes. The object to be sterilized is herein presumed to be housed in a chamber 11 of the sterilizer 100 in a state of being preliminarily wrapped with a wrapping material in order to prevent re-contamination after the sterilization. The wrapping material is, for example, nonwoven fabric of fine mesh, which passes the sterilization gas but barely passes bacteria therethrough. The nonwoven fabric may mainly include resin material such as polyethylene. The wrapping material of this type is sometimes referred to also as a sterilization bag or sterilization wrap.

The sterilizer 100 includes a chamber unit 10, a hydrogen peroxide supply unit 20, an ozone supply unit 30, an exhaustion unit 40, an air introduction unit 50, and a control unit 60.

The chamber unit 10 includes the chamber 11 for housing the object to be sterilized, and peripheral components. The chamber unit 10 includes the chamber 11 having a door 12, a first heater 13, and a first manometer 14.

The chamber 11 is a holder for housing and placing the object to be sterilized therein. The chamber 11 is referred to also as a sterilization container. The chamber 11 is made of stainless steel or an aluminum alloy, and has a structure resistant to a vacuum and decompression. The present embodiment is illustrated below with a case in which a capacity of the chamber 11 is 100 liters (L), for example. The door 12 is arranged on the chamber 11 in an openable manner. The chamber 11 is tightly sealed to prevent vacuum leakage or leakage of the sterilization gas when the door 12 is closed so that the inside of the chamber 11 is decompressed.

The first heater 13 is installed at a circumference of the chamber 11 together with a thermal material to keep the internal temperature of the chamber 11 constant during the sterilization treatment. The temperature of the chamber 11 is measured by a thermometer (not illustrated) arranged at the chamber 11.

The first manometer 14 is a vacuum gauge arranged at the chamber 11 to measure the pressure inside the chamber 11.

The hydrogen peroxide supply unit 20 supplies vapor of hydrogen peroxide to the chamber 11 during the sterilization treatment. The hydrogen peroxide supply unit 20 according to the present embodiment can independently supply the vapor separately produced from two aqueous solutions of hydrogen peroxide. One of the aqueous solutions of hydrogen peroxide is referred to below as a "first aqueous solution", and the other aqueous solution of hydrogen peroxide is referred to below as a "second aqueous solution". A concentration of the hydrogen peroxide contained in the first aqueous solution or the second aqueous solution, or a total amount of the hydrogen peroxide contained in the first aqueous solution or the second aqueous solution is determined according to the presence or absence of a duct part in the object to be sterilized or the material used for the object to be sterilized, as described below. The hydrogen peroxide supply unit 20 includes a bottle 21, an extraction pipe 22, a tube pump 23, a storage part 24, an evaporator 26, and a second heater 29.

The bottle 21 houses the aqueous solution of the hydrogen peroxide. The bottle 21, when exposable, is referred to also as a cartridge. The present embodiment uses the two aqueous solutions of the hydrogen peroxide, and uses a first bottle 21a for housing the first aqueous solution and a second bottle 21b for housing the second aqueous solution.

The extraction pipe 22 extracts the aqueous solutions of the hydrogen peroxide from the respective bottles 21, and supplies the extracted aqueous solutions to the storage part 24. The present embodiment uses a first extraction pipe 22a that extracts the first aqueous solution from the first bottle 21a, and a second extraction pipe 22b that extracts the second aqueous solution from the second bottle 21b.

The tube pump 23 is arranged in the middle of the respective extraction pipes 22 to suck an appropriate amount of the aqueous solutions of the hydrogen peroxide every time out of the respective bottles 21. The present embodiment uses a first tube pump 23a arranged in the middle of the first extraction pipe 22a, and a second tube pump 23b arranged in the middle of the second extraction pipe 22b. The respective extraction pipes 22 may be provided with an optical liquid level sensor (not illustrated), for example. The respective tube pumps 23 suck up the aqueous solutions of the hydrogen peroxide until the liquid level sensor responds, and temporarily stop upon the response of the liquid level sensor and then rotate with a predetermined number of times, so as to supply the predetermined amount of the respective aqueous solutions to the storage part 24.

The storage part 24 is connected to the respective extraction pipes 22 to temporarily store the predetermined amount of the respective aqueous solutions of the hydrogen peroxide sucked out of the bottles 21 before the supply to the evaporator 26. The storage part 24 used may be a semi-transparent fluororesin tube through which the amount of the solution stored inside can be visually confirmed. Since the respective tube pumps 23 can supply the constant amount of the solution stably when driven under an atmospheric pressure, the storage part 24 may be supplied with the air via a first filter 25 so as to be under the atmospheric pressure. The first filter 25 is a high-efficiency particulate air (HEPA) filter, for example.

The evaporator 26 communicates with the storage part 24 via a first supply pipe 27, and evaporates the aqueous solution of the hydrogen peroxide introduced through the storage part 24. The evaporator 26 is, for example, made of stainless steel so as to have resistance to corrosion caused by the hydrogen peroxide, and has a structure resistant to a vacuum and decompression since the evaporator 26 is decompressed simultaneously with the chamber 11.

The first supply pipe 27 is provided with a first electromagnetic valve 70. When the first electromagnetic valve 70 is open, the aqueous solution of the hydrogen peroxide stored in the storage part 24 is sucked and introduced toward the decompressed evaporator 26. Since the storage part 24 is under the atmospheric pressure after being supplied with the air via the first filter 25, the air is also sucked together with the aqueous solution of the hydrogen peroxide. The aqueous solution of the hydrogen peroxide remaining in the storage part 24 and the first supply pipe 27 is also sucked and introduced toward the evaporator 26, so that the constant amount of the vapor of the hydrogen peroxide is stably supplied to the inside of the chamber 11.

The evaporator 26 communicates with the chamber 11 via a plurality of injection pipes 28. The present embodiment uses a first injection pipe 28a and a second injection pipe 28b arranged on a ceiling at two positions in the diagonal line. The first injection pipe 28a is provided with a second electromagnetic valve 71, and the second injection pipe 28b is provided with a third electromagnetic valve 72. When the aqueous solution of the hydrogen peroxide is evaporated in the evaporator 26 to increase the pressure inside the evaporator 26, the second electromagnetic valve 71 or the third electromagnetic valve 72 is opened for a predetermined period of time, so that the vapor of the aqueous solution of the hydrogen peroxide is injected to the inside of the chamber 11. The arrangement of the plural injection pipes 28 as described above can further enhance the uniform diffusion of the vapor inside the chamber 11. The evaporator 26 may be provided with a pressure sensor 39 for determining whether the pressure inside the evaporator 26 is increased to a level within a predetermined range after the injection of the vapor so as to determine whether the predetermined amount of the vapor is supplied from the storage part 24.

The second heater 29 is arranged at a circumference of the evaporator 26 to keep the internal temperature of the evaporator 26 constant. The inside of the evaporator 26 is constantly kept at a predetermined temperature in a range of 65° C. to 120° C., for example.

The ozone supply unit 30 supplies the ozone gas to the chamber 11 during the sterilization treatment. The ozone gas used in the present embodiment is produced inside the ozone supply unit 30. The ozone supply unit 30 includes an oxygen generation device 31, an ozone generator 32, an ozone densitometer 33, a buffer tank 34, and a second manometer 35.

The oxygen generation device 31 produces oxygen ($O_2$) serving as raw material of ozone. The oxygen generation device 31 can adopt a pressure swing adsorption (PSA) mode that causes nitrogen in the air to be adsorbed to an adsorbent such as zeolite to produce oxygen with a high concentration. In particular, the oxygen generation device 31 may be a PSA device having a discharge pressure in a range of about 0.03 to 0.08 MPa as a gauge pressure, and a flowing amount in a range of about 1 to 4 L/min. A pipe connecting the oxygen generation device 31 and the ozone generator 32 is provided with a fourth electromagnetic valve 73. Controlling the open and closed states of the fourth electromagnetic valve 73 as appropriate can regulate the supply amount of the oxygen to the ozone generator 32.

The ozone generator 32 produces the ozone gas from the oxygen produced by the oxygen generation device 31. The ozone generator 32 can adopt a silent discharge mode that applies a high voltage with a high frequency to the oxygen to be discharged and decomposed so as to produce the ozone. The present embodiment is illustrated with a case in which the ozone supply unit 30 includes two ozone generators 32. A production ability of the ozone generators 32 is given by 2 g/hr×two ozone generators=4 g/hr, for example. The ozone generators 32 in this case operate for 1.5 minutes while receiving 1 L/min of the oxygen, so as to produce the ozone with the amount given by 4 g×1.5 minutes/60 minutes=0.1 g. The ozone generators 32 communicate with the buffer tank 34 via a second supply pipe 36.

The ozone densitometer 33 measures a concentration of the ozone gas produced by the ozone generators 32 in the second supply pipe 36. For example, a case is presumed in which a measurement value obtained by the ozone densitometer 33 is 70 g/m³ when the ozone gas is allowed to flow through the second supply pipe 36 for 1.5 minutes with the flowing amount of 1 L/min. The amount of the ozone produced in this case corresponds to the amount given by 1 L/min×1.5 minutes×70 g/1000 L=0.105 g. In addition, a case is presumed in which 0.105 g of the ozone gas is injected to the inside of the chamber 11 with the capacity of 100 L, and the air is further introduced thereto so as to be under the atmospheric pressure. The concentration of the ozone in the chamber 11 in this case corresponds to a volume concentration given by 0.105 g/48 g×22.4 L/100 L×1,000,000=490 ppm, where 48 g is a molecular amount of the ozone, and 22.4 L is the amount of reference gas.

The second supply pipe 36 is provided with a fifth electromagnetic valve 74 between the ozone densitometer 33 and the buffer tank 34. The second supply pipe 36 between the ozone densitometer 33 and the fifth electromagnetic valve 74 may communicate with the exhaustion unit 40 via a piping system X including a sixth electromagnetic valve 75. When the fifth electromagnetic valve 74 is closed and the sixth electromagnetic valve 75 is open, the ozone gas flowing from the respective ozone generators 32 is supplied toward the exhaustion unit 40.

The buffer tank 34 temporarily stores the ozone gas produced by the respective ozone generators 32 before the supply to the evaporator 26. The buffer tank 34 is, for example, made of stainless steel so as to have resistance to corrosion caused by the hydrogen peroxide, and has a structure resistant to decompression. The present embodiment is illustrated below with a case in which a capacity of the buffer tank 34 is two liters (L). The buffer tank 34 communicates with the evaporator 26 via a third supply pipe 37. The third supply pipe 37 is provided with a seventh electromagnetic valve 76. When the ozone gas is injected to the buffer tank 34 while the seventh electromagnetic valve 76 is closed, the pressure inside the buffer tank 34 is transiently increased.

The second manometer 35 is a vacuum gauge arranged at the buffer tank 34 to measure the pressure inside the buffer tank 34. A controller 61 monitors the pressure inside the buffer tank 34 by use of the second manometer 35, so as to confirm whether the ozone injected is increased to a predetermined pressure in the buffer tank 34, or confirm whether leakage or stoppage of the ozone is caused in the second supply pipe 36 or the like.

According to the present embodiment, the ozone gas supplied from the buffer tank 34 is not directly but indirectly injected to the chamber 11 via the evaporator 26. An introduction port of the sterilization gas toward the chamber 11 is shared with the hydrogen peroxide and the ozone gas.

As another embodiment, the ozone gas may be directly injected to the chamber 11 from the buffer tank 34 without bypassing the evaporator 26. The direct injection of the ozone gas to the chamber 11 without bypassing the evaporator 26 has the advantage of increasing the speed of diffusion of the ozone gas inside the chamber 11. This case also has the advantage of increasing the ozone concentration in the chamber 11 when the second electromagnetic valve 71 and the third electric valve 72 arranged between the evaporator 26 and the chamber 11 are closed.

The exhaustion unit 40 vents the atmosphere inside the chamber 11 so as to decompress the inside of the chamber 11 or discharge the gas present inside the chamber 11 to the outside. In particular, the exhaustion unit 40 removes excessive gas from the chamber 11 or the object to be sterilized itself to decompress the inside of the chamber 11 to a medium vacuum level of 100 Pa or below, for example, before the sterilization treatment in order to improve the sterilization effect during the sterilization treatment. The exhaustion unit 40 also eliminates the sterilization gas remaining in the chamber 11 or the object to be sterilized after the sterilization treatment. The exhaustion unit 40 includes a vacuum pump 41, a catalyst tank, and a heater.

The vacuum pump 41 used can be a dry pump such as a scroll pump for medium vacuum, or a hydraulic rotating pump such as a rotary pump. The vacuum pump 41 in the present embodiment is a hydraulic rotating pump. The vacuum pump 41 and the chamber 11 communicate with each other via an exhaustion pipe 38. The exhaustion pipe 38 is provided with an eighth electromagnetic valve 77. When the pressure inside the chamber 11 reaches a predetermined value during the compression, for example, the controller 61 closes the eighth electromagnetic valve 77 to stop the operation of the vacuum pump 41.

The catalyst tank is made of stainless steel, for example, and includes a catalyst such as a pellet type and a honeycomb type. The catalyst mainly includes manganese dioxide, for example, and decomposes the hydrogen peroxide and the ozone. The catalyst tank in the present embodiment is arranged at two positions on the upstream side and the downstream side of the vacuum pump 41 in view of decomposing gas having a risk of corroding the vacuum pump, and also keeping the exhaustion speed as appropriate. A first catalyst tank 42 is a catalyst tank arranged on the upstream side of the vacuum pump 41. A second catalyst tank 43 is a catalyst tank arranged on the downstream side of the vacuum pump 41.

As described above, the ozone supply unit 30 can supply the ozone gas to the exhaustion unit 40 via the piping system X such that the ozone generators 32, the fifth electromagnetic valve 74, and the sixth electromagnetic valve 75 are controlled as appropriate.

The heater keeps the respective catalyst tanks at a temperature in a range of 60° C. to 90° C., for example. A third heater 44 keeps the temperature of the first catalyst tank 42. A fourth heater 45 keeps the temperature of the second catalyst tank 43.

The air introduction unit 50 introduces the air into the inside of the chamber 11. The air introduction unit 50 includes a second filter 51 and a plurality of introduction ports.

The second filter 51 prevents dust in the air from entering the inside of the chamber 11 upon the introduction of the air. The second filter 51 used may be a HEPA filter which is a nonwoven filter of fine mesh, for example.

The respective introduction ports introduce the air through the second filter 51 to the inside of the chamber 11. The introduction ports are preferably arranged at different positions from each other in the chamber 11 in order to equalize the gas concentration inside the chamber 11 simultaneously with the introduction of the air. The present embodiment uses two introduction ports, a first introduction port 52 and a second introduction port 53, for example, arranged on the ceiling at two positions in the diagonal line. The first introduction port 52 is provided with a ninth electromagnetic valve 78. The second introduction port 53 is provided with a tenth electromagnetic valve 79. The controller 61 independently controls the open and closed states of the ninth electromagnetic valve 78 and the tenth electromagnetic valve 79, so as to introduce the air into the inside of the chamber 11 from the different positions at an appropriate timing.

The introduction ports are not limited to those directly arranged at the chamber 11. As another embodiment, the introduction ports may be connected to the chamber 11 via the evaporator 26, or the introduction ports may be connected to the chamber 11 via the buffer tank 34. The introduction ports may also be connected to the chamber 11 via both the evaporator 26 and the buffer tank 34, for example.

The control unit 60 controls the driving operations of power system elements in the respective units included in the sterilizer 100 in accordance with various kinds of operating commands. The control unit 60 includes the controller 61 and a touch panel 62. The controller 61 is electrically connected to the respective power system elements and measurement system elements, for example. The controller 61 controls the operations of the respective power system elements in accordance with a command input via the touch panel 62, a sequence of control operations preliminarily stored, or a detection signal acquired from various types of sensors. The touch panel 62 is electrically connected to the controller 61, and is used by the operator to input the information or command and to visually recognize the information provided from the sterilizer side.

Next, a process of a sterilizing method according to the present embodiment by use of the sterilizer 100 is described below.

FIG. 2 is a flowchart showing the process of the sterilizing method according to the present embodiment. FIG. 3 is a graph showing a change in pressure inside the chamber 11 with a lapse of time through the process of the sterilizing method according to the present embodiment.

The sterilizing method according to the present embodiment includes a treatment mode selection step S100, a preliminary decompression step S200, an ozone adsorption step S300, a sterilization decompression step S400, a sterilization step S500, and an aeration step S700.

Before starting the treatment mode selection step S100, the operator such as a nurse in a hospital places the object to be sterilized wrapped with a wrapping material in the chamber 11, and closes the door 12 to make the inside of the chamber 11 airtight. At this point, the power of the sterilizer 100 is presumed to be already turned on so as to complete a warming-up.

In the sterilization treatment in the present embodiment, the operator can choose a treatment mode depending on the type of the object to be sterilized. The type of the object to be sterilized is classified according to the shape and the material of the object to be sterilized, for example. In particular, the shape of the object to be sterilized may be classified in accordance with the presence or absence of a duct part. The treatment mode selection step S100 is a step of inputting the treatment mode chosen by the operator to the sterilizer 100.

FIG. 4 is a table showing the respective treatment modes executable by the sterilizer 100. The treatment modes may include the following three modes, for example. A short mode is applied to a case in which the object to be sterilized is a medical instrument having no duct part. The medical instrument of this type is a steel product such as a pair of forceps, for example, and is mainly subjected to surface sterilization. A normal mode is applied to a case in which the object to be sterilized is a medical instrument made of resin having a duct part. A long mode is applied to a case in which the object to be sterilized is a medical instrument made of stainless steel having a duct part. The medical instrument of this type is a hard endoscope having a thin tube with an inner diameter of about 1 mm, for example.

The treatment modes differ from each other in the treatment time, the injected amount of the aqueous solution of the hydrogen peroxide, or the number of exposure times in the following steps. The column of the injected amount of the aqueous solution of the hydrogen peroxide in the table shown in FIG. 4 indicates a range of possible values per pulse corresponding to one operation of the sterilization step S500 described below. In particular, the upper row in the column indicates the algebra regarding the injected amount of the first aqueous solution, and the lower row indicates the algebra regarding the injected amount of the second aqueous solution.

The preliminary decompression step S200 is a step executed preliminary to the following ozone adsorption step S300 to decompress the inside of the chamber 11 with respect to the atmospheric pressure. FIG. 3 indicates a period in which the preliminary decompression step S200 is executed by H11. The preliminary decompression step S200 decompresses the inside of the chamber 11 to a level of 100 Pa, for example.

The ozone adsorption step S300 is a step of injecting the ozone gas to the inside of the chamber 11 under the decompressed state obtained by the preliminary decompression step S200 to cause the ozone gas to be adsorbed to the wrapping material wrapping the object to be sterilized. The present embodiment executes an ozone injection step S505 separately from the ozone adsorption step S300. If the ozone adsorption step S300 would not be executed, the ozone gas injected to the inside of the chamber 11 in the ozone injection step S505 would be adsorbed to the wrapping material wrapping the object to be sterilized. The ozone as an adsorbent may prevent the ozone gas sequentially supplied from reaching the object to be sterilized. The present embodiment thus causes the ozone gas to be adsorbed to the wrapping material in the ozone adsorption step S300 before executing the ozone injection step S505 to lead the wrapping material to a saturated state or a state approximate to the saturated state. Preliminarily leading the wrapping material to the saturated state or the state approximate to the saturated state can avoid or decrease the adsorption of the ozone gas to the wrapping material when injecting the ozone gas to the inside of the chamber 11 in the ozone injection step S505, so as to allow the ozone gas to easily reach the object to be sterilized accordingly. Some of the ozone gas injected in the ozone adsorption step S300 reaches the object to be sterilized to contribute to the sterilization, in addition to the ozone gas being adsorbed to the wrapping material.

The execution of the following ozone injection step S505 might be eliminated when the concentration of the ozone gas in the gas supplied to the inside of the chamber 11 is increased in the ozone adsorption step S300. The execution of the ozone adsorption step S300 might be eliminated instead when the concentration of the ozone gas in the gas supplied to the inside of the chamber 11 is increased in the ozone injection step S505. However, the increase in the concentration of the ozone gas as described above might have an unintended influence that would cause deformation of the object to be sterilized, for example, depending on the material used for the object to be sterilized. The series of steps in the sterilizing method according to the present embodiment thus includes the plural steps for injecting the ozone gas to the inside of the chamber 11 several times, so as to avoid or decrease the influence of the ozone gas on the shape or composition of the object to be sterilized more reliably. In view of the decrease in the influence of the ozone gas as described above, the gas to be supplied to the inside of the chamber 11 in the ozone adsorption step S300 is defined to contain the ozone gas with the concentration of about 1%. When the ozone gas is presumed to be produced in the ozone supply unit 30 as described in the present embodiment, the gas to be supplied to the inside of the chamber 11 contains 99% of oxygen excluding the ozone gas. If the concentration of the ozone gas is defined to be higher, the constituent members such as the ozone generators 32 that produce the ozone gas may need to have higher performance. Setting the concentration of the ozone gas to about 1% has the advantage of facilitating the ozone generation by the ozone generators 32. Setting the concentration of the ozone gas to about 1% also has the advantage of avoiding an unintended influence on the object to be sterilized, since the concentration of the ozone gas after the injection to the inside of the chamber 11 can be decreased to 500 ppm or lower.

FIG. 3 indicates the timing of starting the ozone adsorption step S300 by T11. The internal state of the chamber 11 may be kept during a period H12 after the ozone gas is injected to the inside of the chamber 11 in the ozone adsorption step S300, as shown in FIG. 3. For example, when the treatment mode is the short mode, the concentration of the ozone gas in the ozone adsorption step S300 may be about 400 ppm, while the keeping time corresponding to the period H12 may be three minutes. An exposure condition for the ozone gas in this case is approximately given by 400 (ppm)×3 (minutes)=1200 (ppm/min). The control by the controller 61 upon the injection of the ozone gas is the same as the control in the ozone injection step S505 described below. In addition, a preparation step similar to an ozone preparation step S504 described below may be executed before the ozone adsorption step S300.

As illustrated above, the gas supplied to the inside of the chamber 11 in the ozone adsorption step S300 contains a great amount of the oxygen, as compared with the ozone gas. The present embodiment then injects the vapor of the first aqueous solution of the hydrogen peroxide to the inside of the chamber 11 in a first vapor injection step S502. The hydrogen peroxide cannot easily reach the surface of the object to be sterilized when the vapor of the first aqueous solution is injected to the inside of the chamber 11 in the first vapor injection step S502 if a large amount of the oxygen remains inside the chamber 11. The sterilization decompression step S400 is a step executed in view of such a problem to remove the oxygen remaining inside the chamber 11 before the first vapor injection step S502. Decompressing the inside of the chamber 11 in the sterilization decompression step S400 can increase the amount of the hydrogen peroxide reaching the object to be sterilized.

In the sterilization decompression step S400, the controller 61 opens the eighth electromagnetic valve 77 after driving the vacuum pump 41 so as to decompress the inside of the chamber 11 during a period H13 shown in FIG. 3. The controller 61 further opens the second electromagnetic value 71, the third electromagnetic value 72, and the seventh electromagnetic value 76, so as to decompress the inside of each of the evaporator 26 and the buffer tank 34, in addition to the chamber 11. The treatment time indicated in the table shown in FIG. 4 is measured from the point of starting the decompression in this case.

A target pressure in the sterilization decompression step S400 is set to a pressure sufficient to remove the oxygen and lead the vapor of the first aqueous solution of the hydrogen peroxide to reach the object to be sterilized reliably in the following first vapor injection step S502. For example, the target pressure in this case is set to 50 Pa or lower, and particularly preferably set in a range of 25 to 35 Pa.

The controller 61, when the pressure reaches the target pressure, closes the second electromagnetic valve 71, the third electromagnetic valve 72, the seventh electromagnetic valve 76, and the eighth electromagnetic valve 77 to stop the vacuum pump 41. The controller 61 then leads the process to proceed to the sterilization step S500 after the sterilization decompression step S400. The internal state of the chamber 11 may be kept during a period H14 after the sterilization decompression step S400, as shown in FIG. 3.

When the treatment mode is the long mode, the object to be sterilized is a thin tube made of stainless steel, for example. Upon the choice of the long mode, the temperature of the object to be sterilized may be preliminarily increased and kept for a predetermined period of time such as about two minutes while keeping the state of the pressure reached, so as to reduce an influence of water condensation inside the duct part as much as possible.

Figure 5:
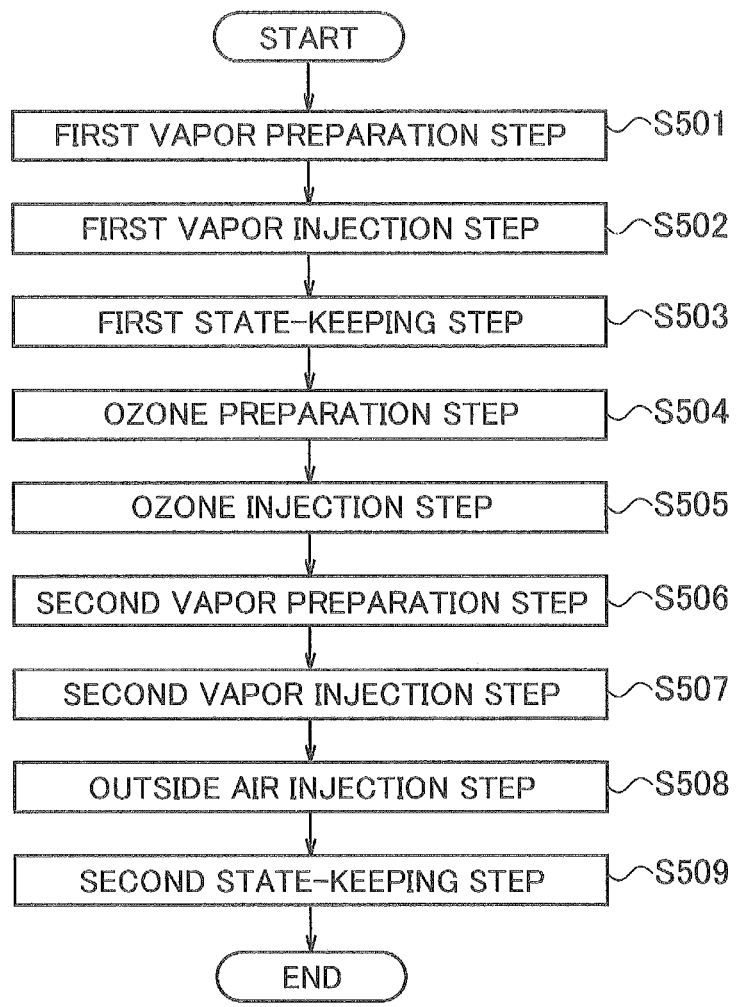
FIG. 5 is a flowchart showing a process of sterilization steps according to the first embodiment.

FIG. 5 is a flowchart showing a process of the sterilization step S500. The sterilization step S500 is a step mainly contributing to the sterilization of the object to be sterilized. The sterilization step S500 includes a first vapor preparation step S501, the first vapor injection step S502, and a first state-keeping step S503.

The first vapor preparation step S501 is a step of producing the vapor of the first aqueous solution to be injected in the following first vapor injection step S502. The controller 61 first rotates the first tube pump 23a to suck the first aqueous solution from the first bottle 21a, and then injects an equally-divided amount of the defined amount of the first aqueous solution to the storage part 24. The defined amount is a total injected amount per pulse, and differs from the respective treatment modes as shown in FIG. 3. For example, when the treatment mode is the short mode, the concentration of the hydrogen peroxide contained in the first aqueous solution is set to a predetermined concentration (x1) in a range of 30% to 60%, and the defined amount is a predetermined amount (y1) in a range of 1 to 4 ml. When the defined amount is divided by two and is then injected, for example, the equally-divided amount of the defined amount is half of y1, which is a predetermined amount (y1/2) in a range of 0.5 to 2 ml. The controller 61 then opens the first electromagnetic valve 70 for a predetermined period of time such as five seconds. Since the inside of the evaporator 26 has been already decompressed, the first aqueous solution is immediately sucked up to the evaporator 26. The air then enters the storage part 24, which communicates with the atmosphere, via the first filter so that the first aqueous solution remaining in the storage part 24 or the first supply pipe 27 is also sent to the evaporator 26. The controller 61 then closes the first electromagnetic valve 70 to evaporate the first aqueous solution in the evaporator 26 for a predetermined period of time such as five seconds. The evaporator 26 is constantly kept at a predetermined temperature in a range of 65° C. to 120° C., for example. When a regulated amount of the first aqueous solution is injected so as to be substantially completely evaporated inside the evaporator 26 with a predetermined value within a capacity in a range of 0.5 to 2 L under a pressure of 50 Pa, for example, the pressure is presumed to be increased to a level of about a saturated vapor pressure. The controller 61 then leads the process to proceed to the first vapor injection step S502 after the first vapor preparation step S501.

The first vapor injection step S502 is a step of injecting the vapor of the first aqueous solution produced by the evaporator 26 to the inside of the chamber 11. FIG. 3 indicates the timing of starting the first vapor injection step S502 by T12. The controller 61 first opens the second electromagnetic valve 71 and the third electromagnetic valve 72 for a predetermined period of time such as ten seconds. The vapor of the first aqueous solution is then strongly injected to the inside of the chamber 11 due to the difference in the pressure. When the object to be sterilized particularly has a duct part, the vapor penetrates the inside of the duct part more easily as the difference in the pressure is higher. In addition, the vapor is easily equalized inside the chamber 11 as described above. The controller 61 then closes the second electromagnetic valve 71 and the third electromagnetic valve 72. The controller 61 repeats the injection of the vapor of the first aqueous solution in the same process in accordance with the respective treatment modes. For example, when the treatment mode is the short mode, the vapor of the first aqueous solution is to be injected to the evaporator 26 per pulse with an amount corresponding to the predetermined concentration (x1) in the range of 30% to 60% to be multiplied by the predetermined amount (y1) in the range of 1 to 4 ml. If a large amount of the first aqueous solution is injected at once, the inside of the evaporator 26 reaches the saturated vapor pressure, which may impede the sufficient evaporation to cause the first aqueous solution to remain in the evaporator 26. In view of this, the controller 61 may divide the amount of the first aqueous solution by two so as to evaporate and sequentially inject the second aqueous solution half-and-half to the chamber 11. The controller 61 may divide the amount of the first aqueous solution into more than two so as to sequentially inject the vapor of the first aqueous solution to the chamber 11. The controller 61 then leads the process to proceed to the first state-keeping step S503 after the first vapor injection step S502.

The first state-keeping step S503 is a step of keeping the vapor of the first aqueous solution in the chamber 11 for a predetermined period of time to sterilize the object to be sterilized. FIG. 3 indicates the predetermined keeping time by H15. The keeping time in the respective treatment modes in this case differs from each other. The keeping time in the short mode is three minutes, for example. The keeping time in the normal mode is four minutes, for example. The keeping time in the long mode is six minutes. The keeping time gradually increases in the order of the short mode, the normal mode, and the long mode.

The sterilization step S500 includes the ozone preparation step S504 and the ozone injection step S505.

The ozone preparation step S504 is a step of producing the ozone gas to be injected in the following ozone injection step S505. The ozone preparation step S504 is not necessarily executed after the completion of the first state-keeping step S503, but is only required to be executed before the start of the ozone injection step S505 so as to prepare the ozone gas. The controller 61 first opens the fourth electromagnetic valve 73 to supply the oxygen with a high concentration to the ozone generators 32. The controller 61 may close the fifth electromagnetic valve 74 and open the sixth electromagnetic valve 75 for several tens of seconds from the start of driving the ozone generators 32, so as to lead the ozone gas to flow through the piping system of the first catalyst tank 42 without supplying the ozone gas to the buffer tank 23 until the concentrations of the oxygen and the ozone are stable. The controller 61 then closes the sixth electromagnetic valve 75 and opens the fifth electromagnetic valve 74, so as to fill the buffer tank 34 with the ozone gas until reaching a predetermined flowing amount, a predetermined concentration, and a predetermined period of time. The controller 61 after finishing filling the buffer tank 34 with the ozone gas closes the fifth electromagnetic valve 74 to stop driving the ozone generators 32.

The ozone injection step S505 is a step of injecting the ozone gas produced in the ozone preparation step S504 to the chamber 11. FIG. 3 indicates the timing of starting the ozone injection step S505 by T13. The ozone injection step S505 is executed after the completion of the first state-keeping step S503. The controller 61 opens the seventh electromagnetic valve 76 and further opens the second electromagnetic valve 71 and the third electromagnetic valve 72 for a predetermined period of time such as five seconds to inject the ozone gas to the chamber 11. The pressure inside the buffer tank 34 is set to a predetermined pressure in a range of about 0.03 to 0.08 MPa to the maximum as a gauge pressure, or a predetermined pressure in a range of about 0.13 to 0.18 MPa as an absolute pressure. The injection of the ozone gas to the inside of the chamber 11 under the decompression of 3000 Pa or less as an absolute pressure is presumed to be completed within about several seconds due to the pressure difference.

The ozone supply unit 30 as described above injects the ozone gas to the inside of the chamber 11 in response to the increase in the pressure of the ozone gas in the buffer tank 34. The above-describe injection of the ozone gas further facilitates the equalization of the diffusion of the ozone gas inside the chamber 11. In addition, the ozone gas easily enters the inside of a tube of the object to be sterilized having a duct part.

The ozone injection step S505 injects the ozone gas to the inside of the chamber 11 through the inside of the evaporator 26, so as to use the ozone gas to push the hydrogen peroxide remaining in the evaporator 26 into the chamber 11 to further improve the sterilization effect. The sterilizer 100 can share the introduction port provided in the chamber 11 to be used as the port to which the hydrogen peroxide is introduced and the port to which the ozone gas is introduced, so as to simplify the circumferential configuration of the chamber 11.

The sterilization step S500 further includes a second vapor preparation step S506, a second vapor injection step S507, an outside air injection step S508, and a second state-keeping step S509.

The second vapor preparation step S506 is a step of producing the vapor of the second aqueous solution to be injected in the following second vapor injection step S507. The second vapor preparation step S506 is not necessarily executed after the completion of the ozone injection step S505, but is only required to be executed before the start of the second vapor injection step S507 so as to prepare the vapor of the second aqueous solution. The generation of the vapor of the second aqueous solution may be executed through a process similar to the generation of the vapor of the first aqueous solution in the first vapor preparation step S501.

The controller 61 first rotates the second tube pump 23b to suck the second aqueous solution from the second bottle 21b, and then injects an equally-divided amount of the defined amount to the storage part 24. For example, when the treatment mode is the short mode, the concentration of the hydrogen peroxide contained in the second aqueous solution is set to a predetermined concentration (x2) in a range of 0.1% to 10%, and the defined amount is a predetermined amount (y2) in a range of 2 to 8 ml. When the defined amount is divided by two and is then injected, for example, the equally-divided amount of the defined amount is half of y2, which is a predetermined amount (y2/2) in a range of 1 to 4 ml. The controller 61 then opens the first electromagnetic valve 70 for a predetermined period of time such as five seconds. Since the inside of the evaporator 26 has been already decompressed, the second aqueous solution is immediately sucked up to the evaporator 26. The air then enters the storage part 24, which communicates with the atmosphere, via the first filter 25 so that the second aqueous solution remaining in the storage part 24 or the first supply pipe 27 is also sent to the evaporator 26. The controller 61 then closes the first electromagnetic valve 70 to evaporate the second aqueous solution in the evaporator 26 for a predetermined period of time such as five seconds. The evaporator 26 is constantly kept at a predetermined temperature in a range of 65° C. to 120° C., for example. When a regulated amount of the second aqueous solution is injected so as to be substantially completely evaporated inside the evaporator 26 with a predetermined value within a capacity in a range of 0.5 to 2 L under a pressure of 50 Pa, for example, the pressure is presumed to be increased to a level of about a saturated vapor pressure. The controller 61 then leads the process to proceed to the second vapor injection step S507 after the second vapor preparation step S506.

The second vapor injection step S507 is a step of injecting the vapor of the second aqueous solution produced by the evaporator 26 to the inside of the chamber 11. FIG. 3 indicates the timing of starting the second vapor injection step S507 by T14. The ozone itself cannot contribute to the sterilization well, but increases the reactivity when moisture is added thereto. The reason for this is presumed that a OH radical or the like is produced when the ozone reacts with moisture or the remaining hydrogen peroxide on surfaces of bacteria so as to effectively destroy cell walls of the bacteria. In view of this, the present embodiment injects the vapor of the second aqueous solution to the inside of the chamber 11 immediately after the completion of the injection of the ozone gas. The hydrogen peroxide contained in the vapor injected to the inside of the chamber 11 is presumed to penetrate cells of the bacteria through the cell walls destroyed by the ozone to attack cell nuclei, so as to improve the sterilization effect.

With regard to the relationship between the first aqueous solution and the second aqueous solution, the concentration of the hydrogen peroxide contained in the second aqueous solution may be lower than or equal to the concentration of the hydrogen peroxide contained in the first aqueous solution.

The injection of the vapor of the first aqueous solution is defined as a main sterilization treatment using the hydrogen peroxide as a material for the sterilization gas. The injection of the vapor of the second aqueous solution is defined as an auxiliary treatment for improving the sterilization efficiency of the sterilization treatment due to the injection of the ozone gas. When the vapor of the second aqueous solution is injected in the second vapor injection step S507, the concentration of the hydrogen peroxide contained in the aqueous solution can be set to be lower for the second aqueous solution than for the first aqueous solution, or set to be equal to each other. This can decrease the used amount of the hydrogen peroxide in the entire sterilization treatment when the sterilizing method according to the present embodiment uses both the first aqueous solution and the second aqueous solution. In addition, the amount of the hydrogen peroxide that may remain on the surface of the object to be sterilized or inside the chamber 11 can be decreased in proportion to the decrease in the used amount of the hydrogen peroxide.

Alternatively, with regard to the relationship between the first aqueous solution and the second aqueous solution, the total amount of the hydrogen peroxide contained in the second aqueous solution may be smaller than or equal to the total amount of the hydrogen peroxide contained in the first aqueous solution.

Setting the total amount of the hydrogen peroxide contained in the second aqueous solution to be smaller than or equal to the total amount of the hydrogen peroxide contained in the first aqueous solution can decrease the used amount of the hydrogen peroxide in the entire sterilization treatment regardless of whether the concentration of the hydrogen peroxide contained in the second aqueous solution is higher than the concentration of the hydrogen peroxide contained in the first aqueous solution.

The concentration of the hydrogen peroxide contained in the first aqueous solution or the second aqueous solution, or the total amount of the hydrogen peroxide contained in the first aqueous solution or the second aqueous solution may be defined in accordance with the presence or absence of a duct part in the object to be sterilized or the material used for the object to be sterilized.

The present embodiment illustrates the three treatment modes that differ from each other in the presence or absence of a duct part in the object to be sterilized or the material used for the object to be sterilized. For example, the object to be sterilized to which the sterilization treatment in the normal mode can be subjected is a thin tube made of resin. The object to be sterilized to which the sterilization treatment in the long mode can be subjected is a thin tube made of stainless steel. With regard to the comparison between the thin tube of resin and the thin tube of stainless steel, the thin tube of stainless steel is typically harder to sterilize than the thin tube of resin. The reason for this is presumed that the reactivity between a transition element such as Fe, Mo, or Cr contained in stainless steel and the hydrogen peroxide is high, and the hydrogen peroxide is thus decomposed in the middle of the treatment to impede the sufficient supply of the hydrogen peroxide to the inside of the thin tube. Another reason for this is presumed that the thin tube of stainless steel has higher thermal conductivity than the thin tube of resin, and is cooled under a decompressed environment more quickly to easily cause water condensation of the hydrogen peroxide inside the thin tube, which impedes the sufficient supply of the hydrogen peroxide to the inside of the thin tube.

When the thin tube of stainless steel is sterilized, for example, the present embodiment can deal with the above-described problem such that the concentration of the hydrogen peroxide contained in the second aqueous solution is set to be higher than the concentration of the hydrogen peroxide contained in the second aqueous solution used in the other treatment modes. The concentration of the hydrogen peroxide contained in the second aqueous solution in this case still does not exceed the concentration of the hydrogen peroxide contained in the first aqueous solution. When the concentration of the hydrogen peroxide contained in the second aqueous solution is equal to the concentration of the hydrogen peroxide contained in the first aqueous solution, the injected amount of the second aqueous solution can be decreased. In other words, the present embodiment, when sterilizing the thin tube of stainless steel, can particularly decrease the entire used amount of the hydrogen peroxide (the concentration of the hydrogen peroxide in the first aqueous solution and the second aqueous solution×the sum of the injected amount of the hydrogen peroxide), as compared with conventional sterilizing methods. The same is also applied to the case in which the total amount of the hydrogen peroxide contained in the second aqueous solution is smaller than or equal to the total amount of the hydrogen peroxide contained in the first aqueous solution, so as to accurately decrease the entire used amount of the hydrogen peroxide (the sum of the total amount of the hydrogen peroxide in the first aqueous solution and the total amount of the hydrogen peroxide in the second aqueous solution).

The sterilization effect is increased as the concentration of the hydrogen peroxide contained in the second aqueous solution is higher. The increase in the concentration of the hydrogen peroxide contained in the second aqueous solution can be presumed to lead to a reduction in the treatment time. The present embodiment is illustrated with a case, when the treatment mode is the long mode, in which the concentration of the hydrogen peroxide contained in the second aqueous solution is set to the predetermined concentration (x1) in the range of 30% to 60% that is equal to the concentration of the hydrogen peroxide contained in the first aqueous solution. While the injected amount per pulse in the short mode or the normal mode is set to the predetermined value (y2) in the range of 2 to 8 ml, the injected amount in the long mode can be set to a smaller predetermined amount (y3) in a range of 1 to 5 ml.

As described above, the second vapor injection step S507 is executed immediately after the completion of the ozone injection step S505. The injection of the vapor of the second aqueous solution may be executed through a process similar to the injection of the vapor of the first aqueous solution in the first vapor injection step S502.

The controller 61 first opens the second electromagnetic valve 71 and the third electromagnetic valve 72 for a predetermined period of time such as ten seconds, and injects the vapor of the second aqueous solution to the chamber 11. The controller 61 then closes the second electromagnetic valve 71 and the third electromagnetic valve 72. The controller 61 repeats the injection of the vapor of the second aqueous solution in the same process in accordance with the respective treatment modes. When the treatment mode is the short mode, the controller 61 in this case may also divide the amount of the second aqueous solution of y2 (2 to 8 ml) by two so as to evaporate and sequentially inject the second aqueous solution half-and-half to the chamber 11, for example. The controller 61 may divide the amount of the second aqueous solution into more than two so as to sequentially inject the vapor of the second aqueous solution to the chamber 11. The controller 61 then leads the process to proceed to the outside air injection step S508 after the second vapor injection step S507.

While the present embodiment is illustrated above with the case of injecting the vapor of the second aqueous solution of the hydrogen peroxide in the second vapor injection step S507, the method may inject vapor produced from water or a solution containing a volatile compound described below, instead of the second aqueous solution. The water used for producing the vapor may be water in which pyrogen is removed or inactivated, or water in which bacteria or microbes are removed or inactivated. The use of the water in which pyrogen is removed or inactivated or the water in which bacteria or microbes are removed or inactivated can preliminarily prevent contamination of the object to be sterilized by pyrogen and the like. The water as used herein may be pure water or ultrapure water such as purified water to which sterilization or disinfection treatment is subjected. The volatile compound may be sodium hypochlorite or alcohols. An example of alcohols may be ethanol. The injection of the solution containing the volatile compound such as sodium hypochlorite or alcohols, which have a disinfection effect, can further improve the sterilization efficiency.

The following is an example of injecting the vapor of the pure water in the second vapor injection step S507, instead of the second aqueous solution, in which the pure water is stored in the second bottle 21b. The pure water is evaporated by the evaporator 26. The use of the pure water instead of the second aqueous solution can also have the advantage of improving the reactivity of the ozone gas, as in the case described above. The table shown in FIG. 4 illustrates the case in which the concentration of the hydrogen peroxide contained in the second aqueous solution in the short mode and the normal mode (x2: a predetermined value in a range of 0.1% to 10%) is greatly lower than the concentration of the hydrogen peroxide contained in the first aqueous solution (x1: a predetermined value in a range of 30% to 60%). In the case in which one of these two treatment modes can be chosen and the sterilization effect is not strictly required for the object to be sterilized, for example, the pure water can be used instead of the second aqueous solution. This can decrease the used amount of the hydrogen peroxide in the entire sterilization treatment.

In the outside air injection step S508 is a step of injecting the outside air that is the atmosphere or dry nitrogen gas to the inside of the chamber 11. FIG. 3 indicates the timing of starting the outside air injection step S508 by T15. The present embodiment is illustrated below with a case in which the outside air is the atmosphere. The outside air injection step S508 is executed immediately after the completion of the second vapor injection step S507. The injection of the air to the inside of the chamber 11 pushes the hydrogen peroxide or the ozone gas congested particularly in the middle of the duct part in the object to be sterilized, so as to further promote the sterilization. The injection of the air to the inside of the chamber 11 also equalizes the distribution of the concentration of the gas present inside the chamber 11 so as to ensure the uniform sterilization. The injection of the air to the inside of the chamber 11 further increases the internal pressure to lead the hydrogen peroxide in the vapor to be slightly condensed on the surface of the object to be sterilized, so as to improve the sterilization effect. The condensation as used herein is referred to also as micro-condensation. Particularly when the outside air is the atmosphere, the cost for the raw material for the gas to be injected can be eliminated, and the configuration for injecting the air to the inside of the chamber 11 can be simplified, so as to reduce the manufacturing costs for the sterilizer 100.

The controller 61 injects the air into the inside of the chamber 11 via the air introduction unit 50. In particular, the controller 61 controls the open and closed states of the ninth electromagnetic valve 78 and the tenth electromagnetic valve 79 as appropriate, so as to regulate the injected amount of the air introduced through the second filter 51. The air is continuously introduced until reaching a predetermined pressure. In the present embodiment, the controller 61 closes the ninth electromagnetic valve 78 and the tenth electromagnetic valve 79 after injecting the air until the pressure inside the chamber 11 reaches about 90 kPa that is about 90% of the atmospheric pressure. The reason for this is that the gas may leak out of the door 12 through the sealing part if the internal pressure of the chamber 11 is equal to the external pressure. The controller 61 then leads the process to proceed to the second state-keeping step S509 after the outside air injection step S508.

As described above, the outside air injection step S508 is effective particularly upon choosing the normal mode or the long mode that is applied to the case in which the object to be sterilized has a duct part. In the case of the short mode for mainly executing the surface sterilization on the object to be sterilized not having a duct part, the outside air injection step S508 is not necessarily executed in view of the simplification of the step when the short mode can ensure the preferable sterilization effect.

The second state-keeping step S509 is a step of keeping the state of the inside of the chamber 11 for a predetermined period of time after the completion of the outside air injection step S508. FIG. 3 indicates the predetermined keeping time by H15. Keeping the state of the inside of the chamber 11 for the predetermined period of time can further promote the sterilization action as described in the outside air injection step S508. The keeping time in the respective treatment modes as used herein differs from each other. The keeping time in the short mode is two minutes, for example. The keeping time in the normal mode is three minutes, for example. The keeping time in the long mode is five minutes, for example.

The sterilization step S500 as described above may be repeated several times as necessary depending on the object to be sterilized. The controller 61 then determines whether the operation of the sterilization step S500 needs to be repeated (step S600) as shown in FIG. 2 after the completion of the second state-keeping step S509. The first operation of the sterilization step S500 is counted as one as the number of the exposure times, and the number of the exposure times in the following steps is indicated by the pulse number. The controller 61, when determining that the sterilization step S500 needs to be repeated (YES), leads the process to proceed to the sterilization decompression step S400 to decompress so as to execute the sterilization step for the second pulse. When determining that no more sterilization step is needed (NO), the controller 61 leads the process to proceed to the following the aeration step S700.

The number of pulses required is defined so as to ensure a sterilization security standard of $10^{-6}$ or lower (SAL< $10^{-6}$). To achieve the standard, the sterilization step in a half cycle corresponding to one pulse needs to annihilate $10^{-6}$ or greater of indicator bacteria. The present embodiment defines two pulses as a full cycle in all of the three treatment modes.

The aeration step S700 is a step of decompressing the inside of the chamber 11 to a predetermined vacuum degree to remove the hydrogen peroxide and the ozone as the sterilization gas, and then injecting the air to reach a level of about the atmospheric pressure so as to dilute the sterilization gas. In the present embodiment, the treatment operation in the aeration step S700 in the short mode differs from the other treatment modes.

First, the aeration step S700 in the case of the treatment mode that is the short mode is described below. The time for the contact between the sterilization gas and the object to be sterilized is shorter for the short mode than for the other modes. The aeration step S700 in this case includes the following treatment step, for example, so as to decrease the treatment time.

The controller 61 first starts operating the vacuum pump 41 and opens the eighth electromagnetic valve 77 to start the decompression of the inside of the chamber 11 immediately after the completion of the second state-keeping step S509 as early as possible. Simultaneously, the controller 61 opens the second electromagnetic valve 71, the third electromagnetic valve 72, and the seventh electromagnetic valve 76, so as to discharge the remaining gas inside the evaporator 26 and the buffer tank 34. The short mode keeps decompressing the inside of the chamber 11 until the internal pressure reaches 100 Pa, for example. The sterilization gas discharged passes through the first catalyst tank 42 and the second catalyst tank 43, so as to lead the hydrogen peroxide to be decomposed to be harmless water and oxygen and lead the ozone to be decomposed to be harmless oxygen to be discharged to the outside of the sterilizer 100 with a concentration of a safety management value or lower. The controller 61 then closes the eighth electromagnetic valve 77 when the pressure inside the chamber 11 reaches a predetermined decompressed pressure.

The controller 61 then opens the ninth electromagnetic valve 78 and the tenth electromagnetic valve 79 to inject the air to the inside of the chamber 11 through the second filter 51. Simultaneously, the controller 61 opens the second electromagnetic valve 71, the third electromagnetic valve 72, and the seventh electromagnetic valve 76 to inject the air also to the inside of each of the evaporator 26 and the buffer tank 34. The injected air diffuses and dilutes the gas remaining inside the chamber 11, and removes the sterilization gas adhering to the object to be sterilized or the inner surface of the chamber 11. The controller 61 keeps injecting the air until the pressure inside the chamber 11 reaches about 90 kPa that is about 90% of the atmospheric pressure, and then closes the ninth electromagnetic valve 78 and the tenth electromagnetic valve 79.

The controller 61 repeats the decompression and the air injection as described above for the prescribed number of times. In the short mode, the total repeated number of times may be three. When the time required for the decompression is presumed to be about three minutes and the time required for the air injection is presumed to be about 0.5 minutes, the aeration step S700 is to take the time given by 3.5 minutes× three times=10.5 minutes. The controller 61 returns the pressure inside the chamber 11 to the atmospheric pressure by the air injection after repeating the decompression and the air injection for the prescribed number of times, and finishes the aeration step S700. The controller 61 ends the sterilization treatment after the aeration step S700.

Second, the aeration step S700 in the case of the treatment mode that is the other modes other than the short mode is described below. The time for the contact between the sterilization gas and the object to be sterilized, and the amount of the hydrogen peroxide adhering to the object to be sterilized or the amount of the hydrogen peroxide remaining inside the chamber 11 are greater for the other modes than the short mode. The aeration step S700 in this case includes the following treatment step, for example.

The fundamental operations of the decompression and the air injection are the same as those in the case in which the treatment mode is the short mode. The pressure reaching upon the decompression, which is set to 100 Pa or lower in the short mode, is set to 50 Pa or lower in the other modes, for example, which is stricter than the case of the short mode, since the object to be sterilized can have a duct part in the other modes.

The controller 61 keeps executing the decompression while injecting the air after the completion of the first decompression and air injection. In particular, the controller 61 starts operating the vacuum pump 41 and opens the eighth electromagnetic valve 77 to start the decompression, and then opens the ninth electromagnetic valve 78 and the tenth electromagnetic valve 79 after a delay of about two seconds, for example, so as to inject the air through the second filter 51. A timing of stopping the air injection at the time of injecting the air after the decompression is presumed to be a point at which the pressure inside the chamber 11 is led to about 90 kPa or greater. A timing of stopping the air injection at the time of decompressing while injecting the air may be set to a point at which the pressure inside the chamber 11 is led to about 90 kPa or lower. The exhaustion during the air injection activates the flow of the air, so as to actively remove the sterilization gas adhering to the object to be sterilized or the inner surface of the chamber 11. In particular, since the object to be sterilized is wrapped with the wrapping material upon the normal sterilization treatment, the sterilization gas adsorbed to the wrapping material can be effectively removed. The time for decompressing while injecting the air is set to about five minutes, for example. The time required for each treatment for the exhaustion during the air injection is shorter than the time required for each treatment for the air injection after the decompression, so as to reduce the entire time necessary for the aeration step S700 accordingly.

The controller 61 further repeats the operations similar to the decompression and the air injection executed first. The repeating time in this case may be two, for example.

The aeration step S700 in this case takes about 15.5 minutes in total, in which the time required for the first decompression and air injection is 3.5 minutes, the time required for decompressing while injecting the air is 5 minutes, and the time required for the second decompression and air injection is 3.5 minutes×2=7 minutes. The controller 61 then returns the pressure inside the chamber 11 to the atmospheric pressure by the air injection, and finishes the aeration step S700. The controller 61 ends the sterilization treatment after the aeration step S700.

While the aeration step S700 repeats the decompression and the air injection several times as described above, which is effective to eliminate the remaining sterilization gas, the treatment time is increased as the repeating number is increased. When the decompression and the air injection are repeated five times, for example, the time (five minutes) shorter than the time (six minutes) taken for repeating two times (three minutes×two times) may be substituted for the next repeating time. This can discharge the sterilization gas remaining inside the chamber 11 more effectively, and further reduce the time required for the aeration step S700.

The treatment time taken for the sterilization treatment according to the present embodiment described above in each treatment mode is substantially as indicated in the table shown in FIG. 3. The operator removes the object to be sterilized from the chamber 11 after the completion of the series of the steps for the sterilization treatment.

The effects achieved by the sterilizing method and the sterilizer 100 that can execute the sterilizing method according to the present embodiment are described below.

The sterilizing method according to the present embodiment for sterilizing the object to be sterilized housed in the chamber 11 includes the ozone preparation step S504 for filling the inside of the buffer tank 34 with the ozone gas. The sterilizing method further includes the ozone injection step S505 for injecting, to the inside of the chamber 11, the ozone gas filled in the buffer tank 34.

The sterilizer 100 according to the present embodiment includes the chamber 11 that houses the object to be sterilized, the ozone generators 32 that produce the ozone gas, and the buffer tank 34 that communicates with the chamber 11 and is filled with the ozone gas produced by the ozone generators 32. The sterilizer 100 further includes the controller 61 that controls the operation of injecting the ozone gas filled in the buffer tank 34 to the inside of the chamber 11.

The sterilizing method and the sterilizer 100 as described above inject the ozone gas as the sterilization gas to the inside of the chamber 11 in the ozone injection step S505 so as to sterilize the object to be sterilized. The use of the buffer tank 34 can allow the ozone gas to be injected to the inside of the chamber 11 in the ozone injection step S505 when the pressure of the ozone gas inside the buffer tank 34 is increased. The injection of the ozone gas upon the increase in the pressure can further enhance the uniform diffusion of the ozone gas inside the chamber 11. When the object to be sterilized has a duct part, for example, the uniform diffusion of the ozone gas can facilitate the entrance of the ozone gas into the duct part of the object to be sterilized.

The present embodiment thus can further reduce the used amount of the ozone gas while keeping the sterilization efficiency. If the buffer tank 34 would not be used, the ozone generators 32 may need to have higher output performance in order to improve the diffusibility of the ozone gas inside the chamber 11, for example, which may require an increase in size of the entire ozone generators 32. The present embodiment using the buffer tank 34 can avoid an increase in size of the ozone generators 32, so as to avoid an increase in size of the sterilizer 100 accordingly.

The sterilizing method and the sterilizer 100 according to the present embodiment can improve the diffusibility of the ozone gas inside the chamber 11 while avoiding an increase in size of the sterilizer 100.

The sterilizing method according to the present embodiment may also include the first vapor preparation step S501 for evaporating and filling the first aqueous solution of the hydrogen peroxide in the evaporator 26, and the first vapor injection step S502 for injecting the produced vapor to the inside of the chamber 11 from the evaporator 26.

The sterilizing method injects the hydrogen peroxide as the sterilization gas to the inside of the chamber 11 in the first vapor injection step S502 so as to sterilize the object to be sterilized. The present embodiment, which uses the hydrogen peroxide in addition to the ozone gas, can further improve the sterilization effect. In the first vapor injection step S502, the vapor of the first aqueous solution is produced by the evaporator 26 and thus can be injected strongly to the inside of the chamber 11 due to the difference in the pressure. When the object to be sterilized has a duct part, for example, the vapor can penetrate the inside of the duct part more easily as the difference in the pressure is higher. The effect of facilitating the equalization of the vapor of the first aqueous solution inside the chamber 11 can also be obtained as in the case described above.

The sterilizing method according to the present embodiment may further include the second vapor preparation step S506 for evaporating and filling the second aqueous solution of the hydrogen peroxide in the evaporator 26, and the second vapor injection step S507 for injecting the produced vapor into the inside of the chamber 11 from the evaporator 26. The second vapor preparation step S506 may use, instead of the second aqueous solution of the hydrogen peroxide, water in which pyrogen is removed or inactivated, water in which bacteria or microbes are removed or inactivated, or a solution containing a volatile compound.

Ozone has the characteristics of increasing the reactivity when moisture is added thereto. The sterilizing method including the second vapor injection step S507 executed after the ozone injection step S505 can improve the sterilization effect more than the case of simply injecting the ozone gas to the inside of the chamber 11. The second vapor injection step S507 preferably uses not only the second aqueous solution but also the water or the solution as listed above. For example, the use of the water in which pyrogen is removed or inactivated or the water in which bacteria or microbes are removed or inactivated can preliminarily prevent contamination of the object to be sterilized caused by pyrogen, bacteria, or microbes.

Second Embodiment

Figure 6:
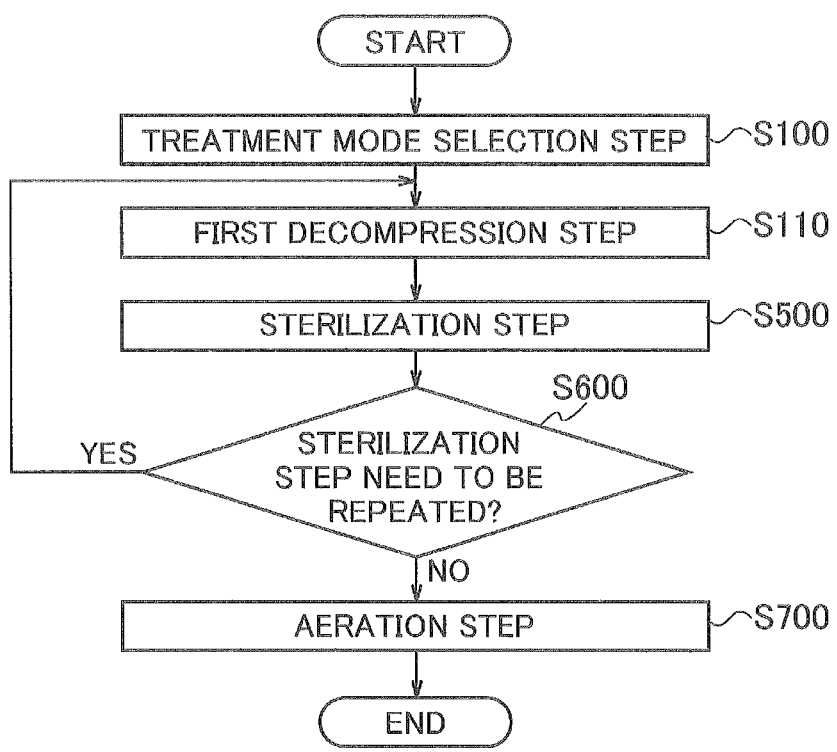
FIG. 6 is a flowchart showing a procedure of a sterilizing method according to a second embodiment.

FIG. 6 is a flowchart showing a process of a sterilizing method according to a second embodiment. The sterilizing method according to the first embodiment includes the ozone adsorption step S300 for causing the ozone gas to be preliminarily adsorbed to the wrapping material wrapping the object to be sterilized. When the adsorption amount of the ozone gas to be adsorbed to the wrapping material when the ozone gas is injected to the inside of the chamber 11 in the ozone injection step S505 can be presumed not to have a great influence on the sterilization efficiency, the ozone adsorption step S300 and further the preliminary decompression step S200 and the sterilization decompression step S400 in relation to the ozone adsorption step S300 executed in the first embodiment may be eliminated in the second embodiment.

As described above, the sterilizing method according to the present embodiment does not employ the preliminary decompression step S200, the ozone adsorption step S300, or the sterilization decompression step S400, as shown in FIG. 6. Instead, the sterilizing method according to the present embodiment additionally includes a first decompression step S110 before the first vapor injection step S502 in the sterilization step S500 since the inside of the chamber 11 still needs to be decompressed. The target pressure set in the first decompression step S110 and the control executed by the controller 61 until reaching the target pressure may be the same as those described in the sterilization decompression step S400.

The sterilizing method and the sterilizer 100 according to the present embodiment are described below in reference to Example in comparison with two comparative examples.

FIG. 7 is a table showing various kinds of conditions for sterilization treatment tests executed for Comparative Example 1 and Comparative Example 2, in addition to Example according to the present embodiment. FIG. 8 is a table showing results of each test executed under the conditions shown in FIG. 7. FIG. 8 shows a negative rate for each test. The column on the left side of the negative rate indicates the number of biological indicators used as described below that show the negative rate. The respective tests were executed for three days, and the respective values in parentheses in the column of the negative rate indicate the test results obtained in each day.

The respective tests use strip-type biological indicators (BIs) suitable for mainly evaluating the surface sterilization for the object to be sterilized for ease of comparison of the sterilization effect. In particular, the BI used in each test is HMV-091-type available from APEX (bacterium number: ATCC12980, $21 \times 10^6$ cfu/disc, D value: 1.0 min). The term "D value" refers to a time necessary for annihilating 90% of test bacteria and decreasing a survival rate to one tenth. Three to five BIs are exposed per test. Since the BIs used are not a thin tube having a duct part, the step of the air injection corresponding to the outside air injection step S508 in the present embodiment is omitted so as to facilitate the comparison particularly between Example and Comparative Example 1.

A chamber used in each test is presumed to have the same structure under the same conditions as the chamber 11 described above. In particular, the capacity of the chamber 11 is 100 L, and is preliminarily heated to 50° C. Only the BIs are preliminarily housed in the chamber 11. The other test conditions are as shown in FIG. 8. The injected amount of the aqueous solution of the hydrogen peroxide injected in the first time (referred to below as a "first aqueous solution" in all the tests for illustration purposes) is set to be the same in all the tests for ease of comparison.

Figure 9:
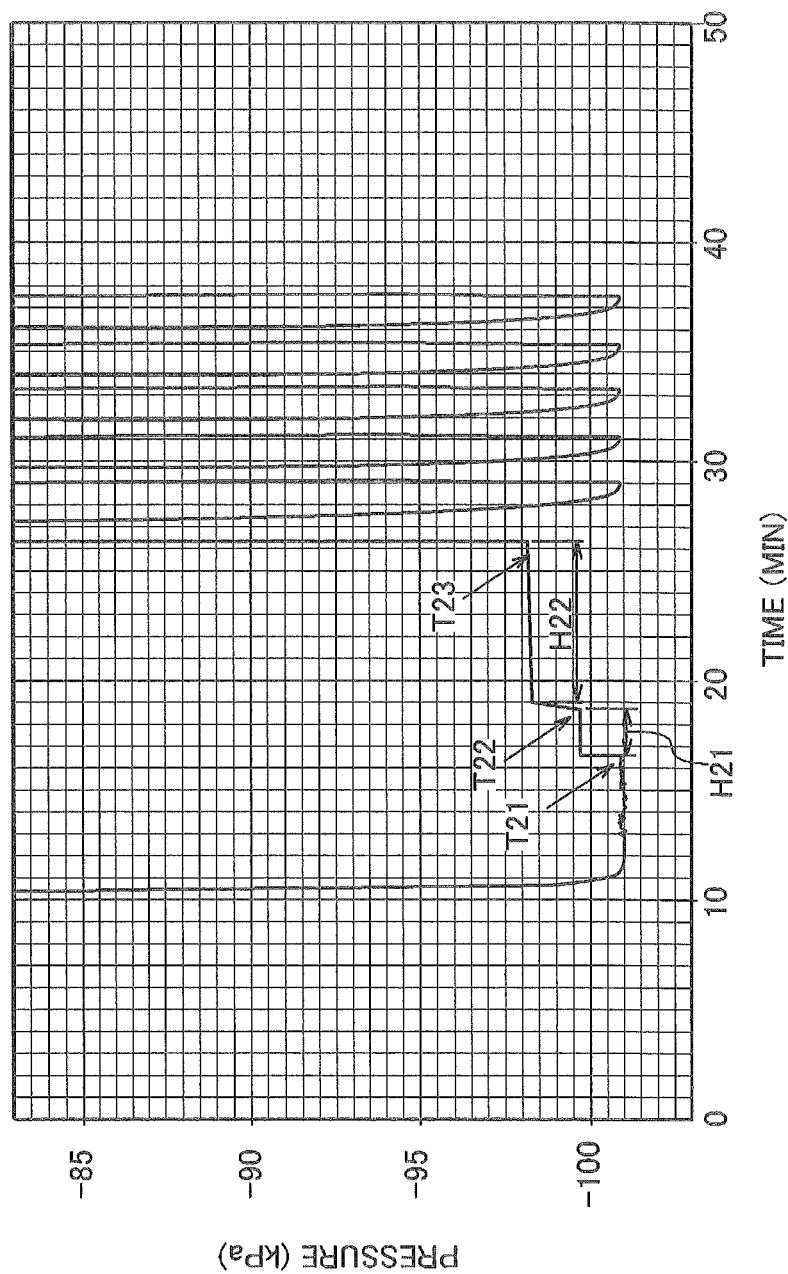
FIG. 9 is a graph showing a change in pressure inside the chamber in a case of Comparative Example 1.

FIG. 9 is a graph showing a change in pressure inside the chamber 11 in Comparative Example 1. The sterilization step in Comparative Example 1 simulates the sterilizing method disclosed in Patent Literature 1. In Comparative Example 1, the vapor of the first aqueous solution is injected to the inside of the chamber 11 at a timing T21 after the decompression, and is kept during a period H21. The ozone gas is then injected to the inside of the chamber 11 at a timing T22, and is kept during a period H22. The aeration step is finally executed at a timing T23.

Figure 10:
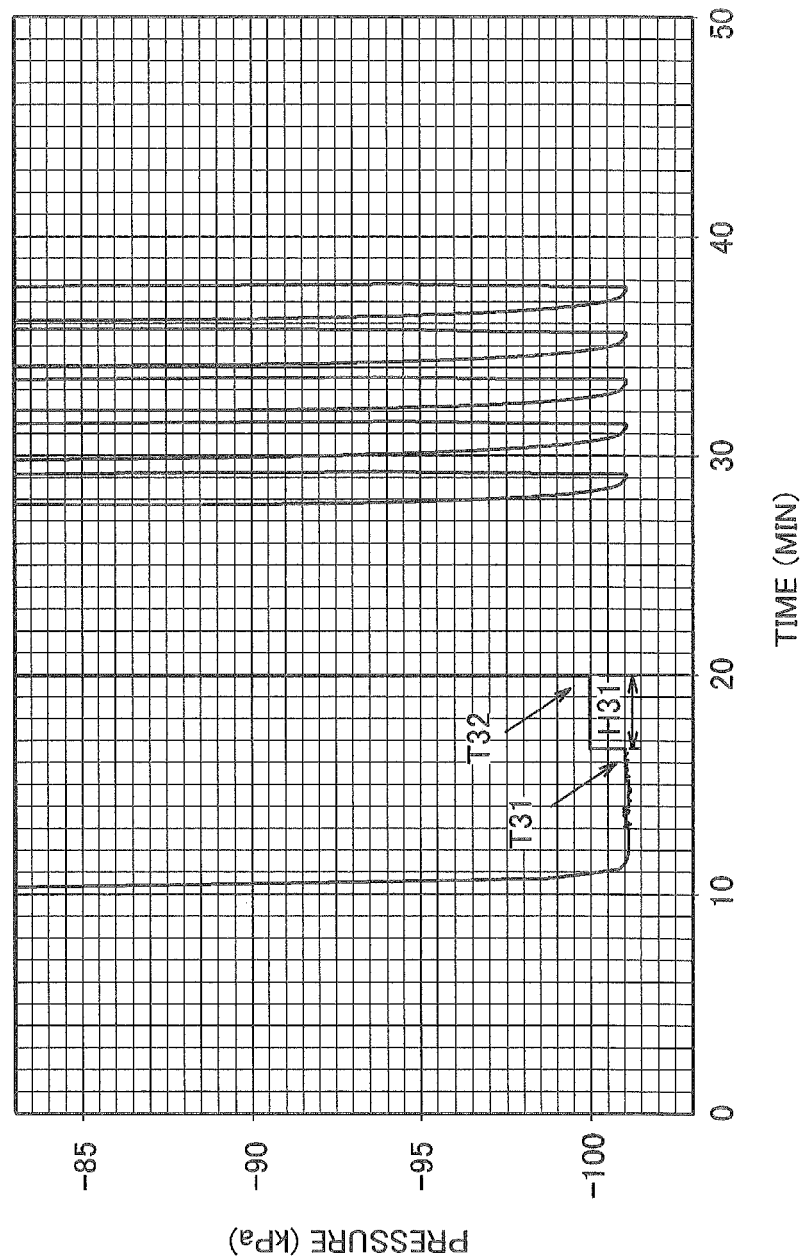
FIG. 10 is a graph showing a change in pressure inside the chamber in a case of Comparative Example 2.

FIG. 10 is a graph showing a change in pressure inside the chamber 11 in Comparative Example 2. The sterilization step in Comparative Example 2 does not execute the injection of the ozone gas. In Comparative Example 2, the vapor of the first aqueous solution is injected to the inside of the chamber 11 at a timing T31 after the decompression, and is kept during a period H31. The air is then injected to the inside of the chamber 11 at a timing T32. The aeration step is finally executed.

Figure 11:
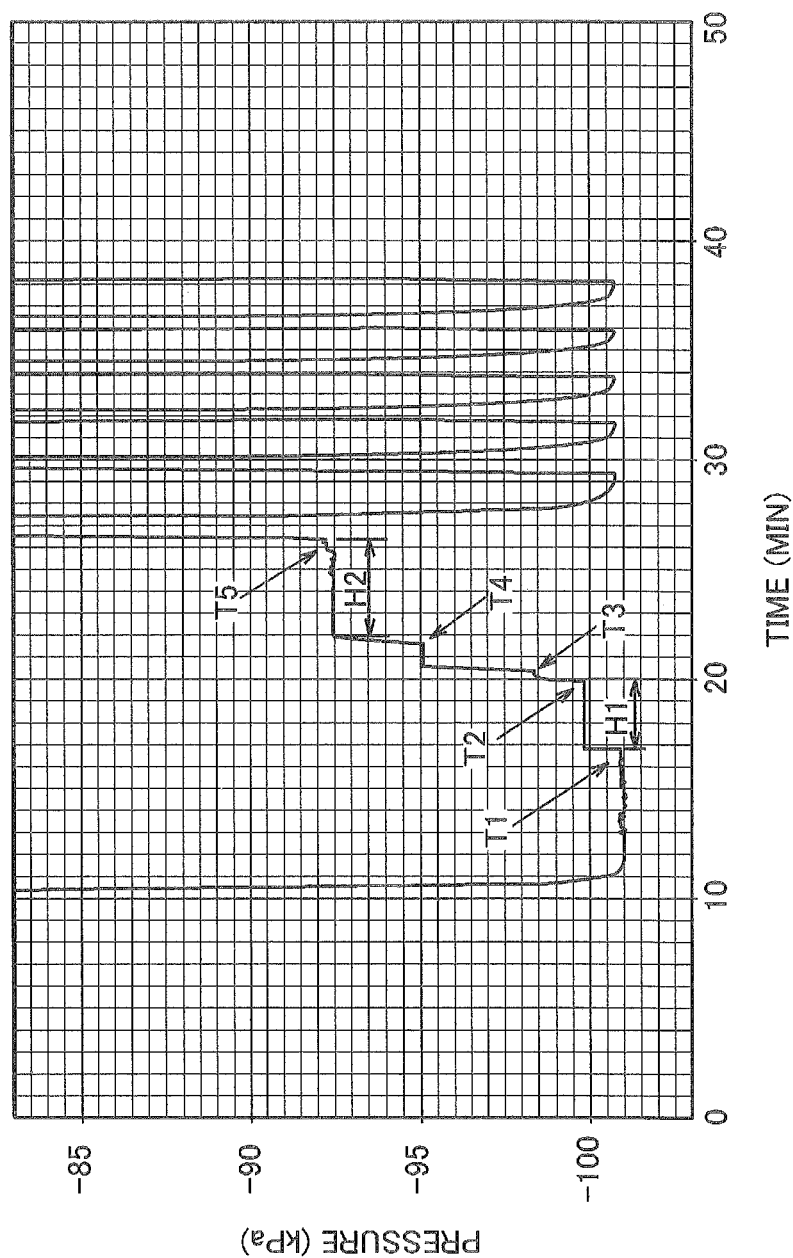
FIG. 11 is a graph showing a change in pressure inside the chamber in a case of Example.

FIG. 11 is a graph showing a change in pressure inside the chamber 11 in Example. In Example, the vapor of the first aqueous solution is injected to the inside of the chamber 11 at a timing T1 after the decompression (the first vapor injection step S502), and is kept during a period H1 (the first state-keeping step S503). The ozone gas is then injected to the inside of the chamber 11 at a timing T2 (the ozone injection step S505). The vapor is continuously injected to the inside of the chamber at a timing T3 and a timing T4 (the second vapor injection step S507), and is kept during a period H2 (the second state-keeping step S509). While the sterilization step is illustrated above with the case of injecting the vapor of the second aqueous solution in the second vapor injection step S507, Example uses the vapor of pure water as an example of not having the sterilization effect when assumed to be used independently. The aeration step is finally executed at a timing T5.

The results of the respective tests revealed that, as shown in FIG. 8, upon the comparison of the negative rate in each test, Example has the higher negative rate than Comparative Example 1 or Comparative Example 2, showing that Example has the higher sterilization effect than Comparative Example 1 or Comparative Example 2.

The sterilizing method as described above can reduce the time corresponding to the ozone adsorption step S300, when omitted, and still avoid a decrease in the sterilization effect regardless of the omission of the ozone adsorption step S300, so as to further decrease the operating time of the sterilizer 100 for executing the sterilizing method.

It should be understood that the present disclosure includes various embodiments not described herein.

REFERENCE SIGNS LIST

11 CHAMBER
26 EVAPORATOR
32 OZONE GENERATOR
61 CONTROLLER
100 STERILIZER

The invention claimed is:

1. A sterilizing method for sterilizing a sterilization object housed in a chamber, the method comprising:
   a first vapor preparation step of evaporating a first aqueous solution of hydrogen peroxide and filling produced vapor in an evaporator;
   a first vapor injection step of injecting the produced vapor to the inside of the chamber from the evaporator;
   an ozone preparation step of filling an inside of a buffer tank with ozone gas; and
   an ozone injection step of injecting the ozone gas filled in the inside of the buffer tank to an inside of the chamber,
   wherein the ozone injection step injects the ozone gas filled in the inside of the buffer tank via the evaporator after the first vapor injection step, thereby forcing a portion of the produced vapor of the hydrogen peroxide remaining in the evaporator into the chamber.

2. The sterilizing method according to claim 1, further comprising:
   a second vapor preparation step of evaporating and filling, in the evaporator, a second aqueous solution of hydrogen peroxide, water in which pyrogen is removed or inactivated, water in which bacteria or microbes are removed or inactivated, or a solution containing a volatile compound; and
   a second vapor injection step of injecting produced vapor to the inside of the chamber from the evaporator.

* * * * *